United States Patent
DeFreitas et al.

(10) Patent No.: US 9,332,947 B2
(45) Date of Patent: May 10, 2016

(54) X-RAY MAMMOGRAPHY AND/OR BREAST TOMOSYNTHESIS USING A COMPRESSION PADDLE WITH AN INFLATABLE JACKET WITH DUAL BOTTOM LAYER JOINED AT A SEAM ENHANCING IMAGING AND IMPROVING PATIENT COMFORT

(71) Applicant: Hologic, Inc., Bedford, MA (US)

(72) Inventors: Kenneth DeFreitas, Patterson, NY (US); Ian Shaw, Yorktown Heights, NY (US); Timothy R. Stango, Sandy Hook, CT (US)

(73) Assignee: HOLOGIC, INC., Bedford, MA (US)

(*) Notice: Subject to any disclaimer, the term of this patent is extended or adjusted under 35 U.S.C. 154(b) by 285 days.

(21) Appl. No.: 13/679,446

(22) Filed: Nov. 16, 2012

(65) Prior Publication Data

US 2013/0129039 A1 May 23, 2013

Related U.S. Application Data

(60) Provisional application No. 61/561,620, filed on Nov. 18, 2011.

(51) Int. Cl.
*A61B 6/04* (2006.01)
*A61B 6/00* (2006.01)
*A61B 6/02* (2006.01)

(52) U.S. Cl.
CPC . *A61B 6/04* (2013.01); *A61B 6/502* (2013.01); *A61B 6/025* (2013.01)

(58) Field of Classification Search
CPC .. A61B 6/0421; A61B 6/0414; A61B 6/0435; A61B 5/708; A61B 2019/205

USPC ................................................ 378/37
See application file for complete search history.

(56) References Cited

U.S. PATENT DOCUMENTS

| | | | |
|---|---|---|---|
| 4,567,899 A * | 2/1986 | Kamens et al. | 600/493 |
| 6,577,702 B1 * | 6/2003 | Lebovic et al. | 378/37 |
| 6,587,578 B2 | 7/2003 | Godik et al. | |
| 6,682,484 B1 | 1/2004 | Entrekin et al. | |
| 6,765,984 B2 | 7/2004 | Higgins et al. | |
| 6,850,590 B2 | 2/2005 | Galkin | |
| 6,968,033 B2 | 11/2005 | Lebovic et al. | |
| 6,975,701 B2 | 12/2005 | Galkin | |
| 7,489,761 B2 | 2/2009 | Defreitas et al. | |
| 7,505,555 B2 | 3/2009 | Hermann et al. | |
| 7,512,211 B2 | 3/2009 | Galkin | |
| 7,639,780 B2 | 12/2009 | Minyard | |
| 7,792,244 B2 | 9/2010 | DeFreitas et al. | |
| 7,822,457 B2 | 10/2010 | Lokhandwalla et al. | |
| 2003/0007598 A1 | 1/2003 | Wang et al. | |
| 2003/0099325 A1* | 5/2003 | Galkin | 378/37 |
| 2004/0156472 A1* | 8/2004 | Galkin | 378/37 |
| 2005/0113683 A1* | 5/2005 | Lokhandwalla et al. | 600/427 |

(Continued)

OTHER PUBLICATIONS

International Search Report, PCT/US2012/065546, dated Feb. 5, 2013.

(Continued)

*Primary Examiner* — Nicole Ippolito
*Assistant Examiner* — Sean Luck

(57) ABSTRACT

A system and method using an inflatable jacket over the compression paddle of a mammography and/or tomosynthesis system to enhance imaging and improve patient comfort in x-ray breast imaging.

27 Claims, 3 Drawing Sheets

(56) References Cited

U.S. PATENT DOCUMENTS

| | | |
|---|---|---|
| 2006/0050844 A1 | 3/2006 | Galkin |
| 2006/0165215 A1* | 7/2006 | Galkin ............................ 378/37 |
| 2007/0280412 A1* | 12/2007 | Defreitas et al. ................ 378/37 |
| 2008/0240345 A1* | 10/2008 | Galkin ............................ 378/37 |
| 2008/0247508 A1 | 10/2008 | Harrington |
| 2009/0003519 A1* | 1/2009 | Defreitas et al. ................ 378/37 |
| 2009/0135997 A1 | 5/2009 | DeFreitas |

OTHER PUBLICATIONS

Supplementary European Search Report, EPApp 12849236.0, dated May 15, 2013.

\* cited by examiner

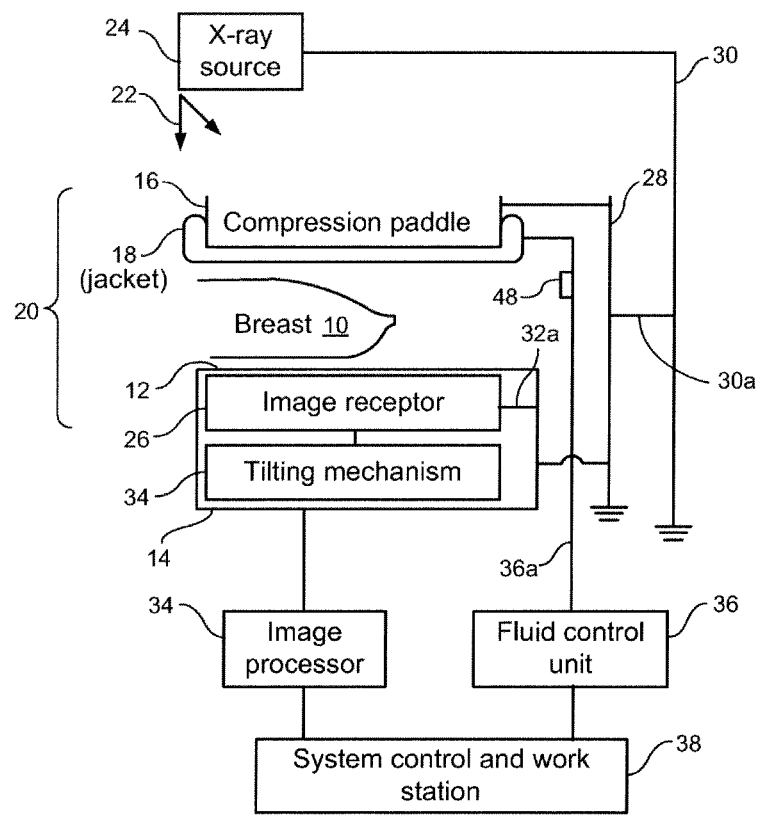
F I G. 1

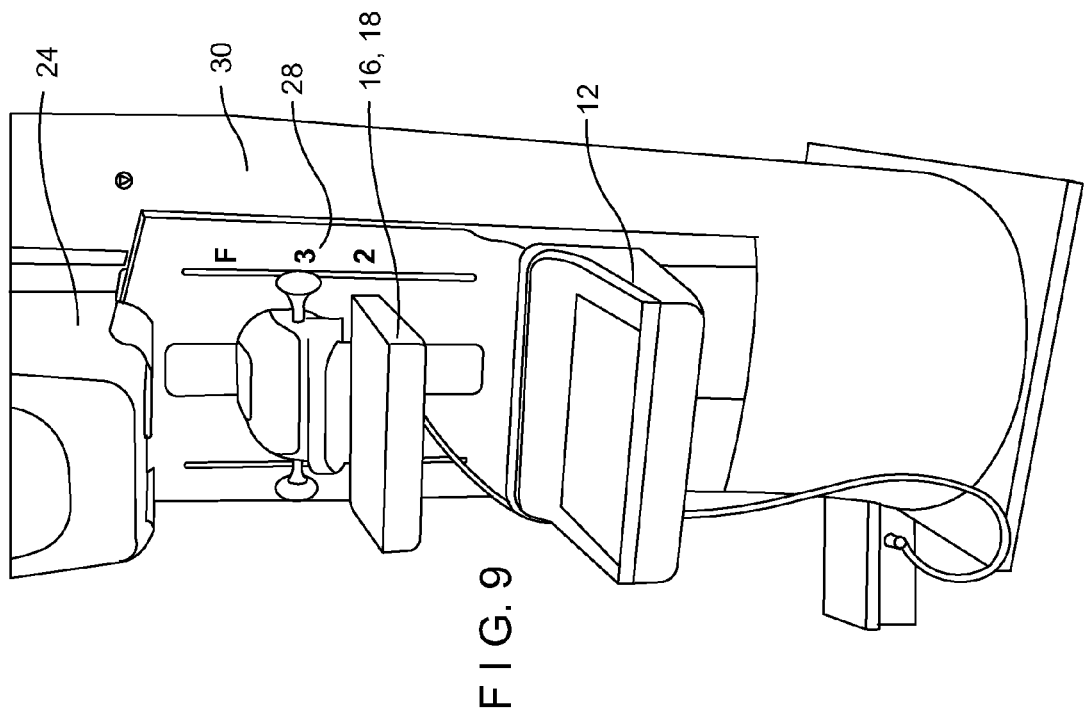
FIG. 7
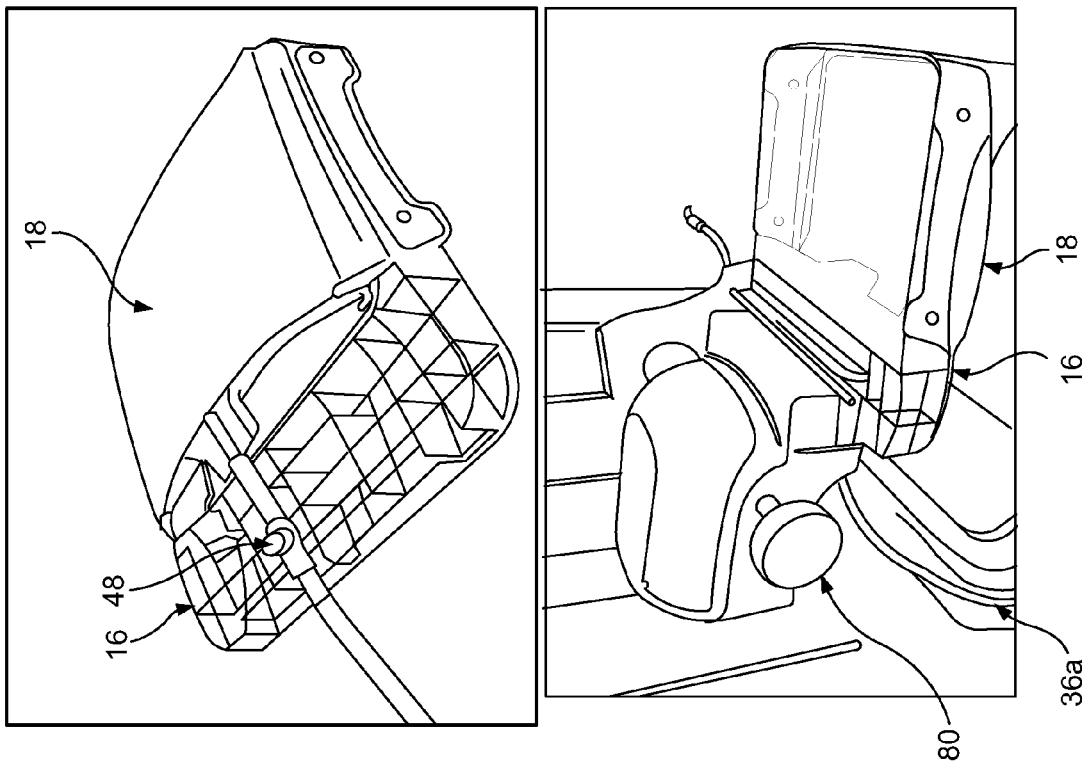
FIG. 8
FIG. 9

X-RAY MAMMOGRAPHY AND/OR BREAST TOMOSYNTHESIS USING A COMPRESSION PADDLE WITH AN INFLATABLE JACKET WITH DUAL BOTTOM LAYER JOINED AT A SEAM ENHANCING IMAGING AND IMPROVING PATIENT COMFORT

FIELD

This patent specification pertains to mammography and/or breast tomosynthesis using an inflatable compression paddle jacket that improves patient comfort and imaging results.

BACKGROUND AND SUMMARY OF THE DISCLOSURE

A significant patient concern in mammography and breast tomosynthesis is the discomfort the patient may feel when the breast is compressed, typically between two rigid plastic surfaces, with sufficient force to immobilize the breast and spread out the breast tissues for x-ray imaging. Another significant challenge is to ensure that the imaged field include the desired amount of breast tissue. The reasons for using compression include: (1) to make the breast thinner in the direction of x-ray flux and thereby reduce patient radiation exposure from the level required to image the thicker parts of a breast that is not compressed; (2) to make the breast more uniform in thickness in the direction of x-ray flux and thereby facilitate more uniform exposure at the image plane over the entire breast image; (3) to immobilize the breast during the x-ray exposure and thereby reduce image blurring; and (4) to bring breast tissues out from the chest wall into the imaging exposure field and thus image more tissue. As the breast is being compressed, typically a technician manipulates the breast to position it appropriately and counter the tendency that compression has of pushing breast tissue toward the chest wall and out of the image field.

Standard compression methods for mammography and tomosyntesis use a movable, rigid clear plastic compression paddle. The breast is placed on a breast platform that typically is flat, and the paddle is then compressed onto the breast, usually while a technician or other health professional is holding the breast in place and perhaps manipulates the breast to ensure proper tissue coverage in the image receptor's field of view and to help spread the breast.

One reason for discomfort that the patient may feel is that the compression force is non-uniformly distributed throughout the breast. It is concentrated at the thickest portion of the breast, usually near the chest wall, at or near the lower front edge of the compression paddle and the upper front corner of the breast platform. The anterior portion of the breast, such as near the nipple, may receive less compressive force, or no compression force. The paddle may not even contact this portion of the breast. (The terms front, lower and upper pertain to using a CC imaging orientation, with the patient facing the front of the imaging system, although it should be understood that other imaging orientations, including MLO, are used with the same equipment and these terms need to be adjusted accordingly.)

Some systems improve patient comfort by providing compression paddles that tilt as the breast is being compressed. A tilting paddle arrangement is available in various paddle sizes from Lorad of Danbury, Conn., a division of the assignee hereof, Hologic, Inc. of Bedford, Mass., under the trade name F.A.S.T. (of FAST). This tilting paddle provides more uniform compression across the breast, and more comfortable breast examinations.

Other methods for improving patient comfort have been proposed and some have been in clinical use to improve patient comfort. One is the use of relatively thin foam pads that are placed above and/or below the breast. The pad deforms to some extent during the compression procedure and may provide improved comfort by spreading out the pressure to a greater extent than using a hard-surfaced paddle and/or breast platform alone. One such pad system is discussed in commonly owned U.S. Pat. Nos. 6,968,033, 6,765, 984, 6,577,702, and 7,505,555, and published U.S. patent application US 2003/0007597 A1. Another pad system is proposed in U.S. Pat. Nos. 6,850,590 and 6,975,701 and published U.S. patent applications US 2006/0050844 A1, US 2004.0156472 A1 and US 2003/0099325 A1, all naming as the inventor Benjamin M. Galkin Such pads are not transparent to visible light. As a result, if such a pad is between the breast and the compression paddle, the breast will not be visible through the paddle, and this can impair the technician's effort to position and manipulate the breast during compression. The pad needs to be made of fairly dense thin form, so as to provide meaningful deformability when compressed under or above the breast. If the foam pad slips during positioning and as a result does not cover the entire imaging field, an edge of the pad may cause image artifacts.

Another system for improving patient comfort has been proposed for a different purpose—to immobilize the breast during biopsy—by Scientific Biopsy (www.sbiopsy.com). It is understood to use a soft, trough-shaped support to cradle the breast and a flexible band that wraps over the breast to impose a holding force. A thin plastic sheet compressing a breast for ultrasound examination rather than for x-ray imaging is proposed in published patent application US 2003/0007598 A1 (see, e.g., FIG. 7 and paragraph [0115]) but no teaching could be found that the material is transparent to visible light or that the arrangement is useful for x-ray imaging or with a flat breast platform. U.S. Pat. No. 6,682,484 discusses the use of a polymeric membrane stretched under tension to restrain the breast during sonographic and/or x-ray imaging. U.S. Pat. No. 7,822,457 discusses the use of tensioned membrane to compress the breast for medical imaging, and that the membrane may be tensioned with a mechanical device or by means of an inflatable bladder. U.S. Pat. No. 6,587,578 discusses a non-rigid object holder comprising a resilient membrane attached to a first member to form an inflatable component for holding the object to be examined between the inflatable component and a base support.

Commonly assigned U.S. Pat. Nos. 7,489,761 and 7,792,244 describe (1) placing a fluid-filled pillow or bag between the compression paddle and the breast before the breast is compressed, (2) compressing the breast with a sheet of a material such as Mylar stretched or at least supported between two rods or rollers (instead of using a conventional compression paddle), and (3) using a paddle provided with a lining of concave compressible material.

All of the patents and applications identified above are hereby incorporated by reference in this patent specification as though they are fully set forth herein.

While at least some of the systems mentioned above are believed to have advantageous features, it is believed that a need still remains to further improve breast imaging and patient comfort. This patent specification is directed to new approaches to address challenges in breast imaging and particularly x-ray breast imaging.

One non-limiting example of such new approaches in mammography and/or breast tomosynthesis involves the use of a specially adapted device to control, distribute and redirect breast compression forces. Preferably, the device comprises an inflatable jacket for the compression paddle.

In a non-limiting example, an x-ray breast imaging system that uses the new approach comprises a data acquisition unit in which an x-ray source selectively emits an imaging x-ray beam, an image receptor receives the beam and produces x-ray imaging information in response thereto, and a breast immobilizer that is between the source and the receptor. The immobilizer comprises a breast platform configured to support a patient's breast for imaging with said beam and a compression paddle supported for movement toward the breast platform to compress the breast and away from the breast platform to release the breast. The compression paddle has a front wall configured to be adjacent the patient's chest wall when the patient's breast is supported for imaging, side walls extending transversely to the front wall, and an underside facing the breast platform. A paddle jacket is removably secured to the compression paddle. Typically, the jacket has a double thickness bottom that extends along the underside of the paddle when secured to the paddle and forms an inflatable chamber. A fluid conduit extends from the chamber to a device to inflate the chamber. Typically, there is a quick-attach coupling between the conduit and the chamber, so that the chamber can be in fluid-flow communication with a fluid control unit that selectively supples fluid to the chamber to selectively inflate the chamber. An image processor coupled with the image receptor is configured to receive imaging information and produce x-ray images. A workstation and system control unit is configured to control system operations thereof in response to operator inputs.

The compression paddle jacket typically has front and side walls extending along the front and side walls of the compression paddle, respectively, and can be releasably secured to the compression paddle in any one of a number of different ways. In one example, one or more of the jacket's front and side walls comprise clipping members configured to releasably clip upper portions of one or more of the front and side walls of the compression paddle. In another example, the jacket's bottom and, if desired, the front and side walls as well, adhesively adhere to the compression paddle. An exterior portion of one or more of the front wall and bottom of said jacket can include a friction-enhancing surface configured to enhance friction with the patient's skin. The friction enhancing surface can comprise a surface with a sticky substance therein or thereon.

The jacket bottom preferably is substantially transparent to visible light, whereby a technician adjusting a patient's breast for imaging can visualize the breast through said jacket. A non-limiting example of jacket material is vinyl. The jacket bottom can include markings of a material that attenuates the x-ray beam sufficiently to make the markings visible or at least detectable in said x-ray images. The jacket's inflatable chamber in divided into two or more sub-chambers that are inflatable to different pressures. In one example, the jacket can be made of two layers of flexible sheet material that are seamed at least at a portion that extends along a junction between the front wall and the underside of the compression paddle.

In one example of breast imaging, a technician secures the inflatable jacket to the compression paddle and makes a connection between the jacket chamber and a fluid conduit. With the patient's breast on the breast platform, the technician lowers the paddle to compress the breast while manipulating breast tissue, and inflates the jacket's chamber to a pressure that achieves a desired compression and spreading of breast tissue. The immobilized breast is imaged in the desired imaging mode. Typically, a new paddle jacket is used for each patient, so the technician disconnects the fluid flow connection and disposes of the used jacket. The inflation and deflation can be operator-powered, such as by a hand or foot operated pump, with appropriate operator-controlled valves, or powered under operator control using suitable electric or other pumps controlled by buttons or other interface devices or under computer control triggered by the operator or by positioning the paddle relative to the breast (e.g., inflating when the paddle has reached a certain position or acts on the breast with w certain force).

BRIEF DESCRIPTION OF THE DRAWINGS

FIG. 1 is a partly schematic view and partly a block diagram of a mammography and/or tomosynthesis system using an inflatable or inflated paddle jacket in imaging a patient's breast with x-rays.

FIG. 7 is a perspective view of an inflatable jacket secured to a compression paddle (upside down).

FIG. 8 illustrates a compression paddle with an inflatable jacket secured thereto, and with the combination secured to a breast imaging system.

FIG. 9 illustrates a breast imaging system using an inflatable jacket over the compression paddle.

DETAILED DESCRIPTION OF PREFERRED EMBODIMENTS

Figure 2:
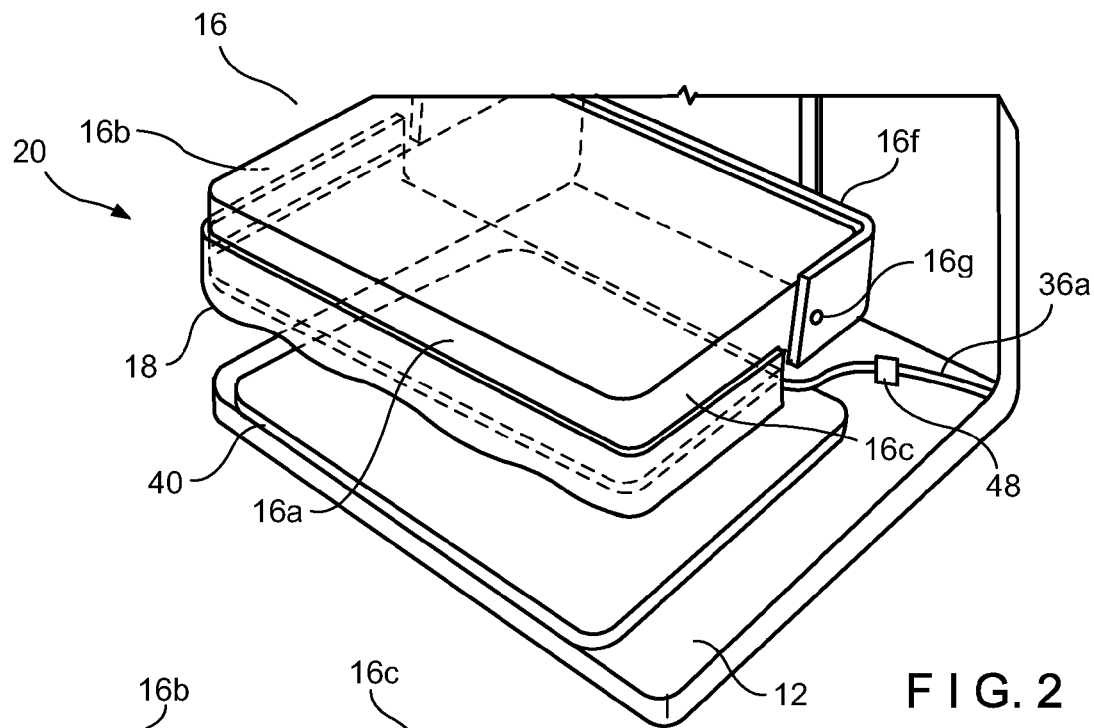
FIG. 2 is a partial perspective view, not to scale, which illustrates a compression paddle provided with an inflatable or inflated jacket and a breast platform with a compressible mat thereon, as a part of an x-ray mammography and/or tomosynthesis system.

Referring to FIG. 1, a patient's breast 10 is immobilized for x-ray imaging between a breast platform 12 and a compression paddle 16. Platform 12 can be the upper surface of a housing 14. At least an underside of compression paddle 16 is covered with an inflatable paddle jacket 18. Platform 12 and paddle 16 form a breast immobilizer unit 20 that is in a path of an imaging beam 22 emanating from x-ray source 24. Beam 22 impinges on image receptor 26 that is in housing 14. Immobilizer 20 and housing 14 are supported on an arm 28. X-ray source 24 is supported on an arm 30. For mammography, support arms 28 and 30 can rotate as a unit about an axis such as at 30a between different imaging orientations such as CC and MLO, so that the system can take a mammogram projection image Mp at each orientation. Image receptor 26 remains in place relative to housing 14 while an image Mp is taken. Immobilizer 20 releases breast 10 for movement of arms 28 and 30 to a different imaging orientation. For tomosynthesis, support arm 28 stays in place, with breast 10 immobilized and remaining in place, while at least source support arm 30 rotates source 24 relative to immobilizer 20 and breast 10 about an axis such as 30a. The system takes plural tomosynthesis projection images of breast 10 at respective angles of beam 22 relative to breast 10. Concurrently, image receptor 26 may be tilted relative to breast platform 12 in sync with the rotation of source support arm 30. The tilting can be through the same angle as the rotation of source 24, but preferably is through a different angle, selected such that beam 22 remains substantially in the same position on image receptor 26 for each of the plural images Tp. The tilting can be about an axis 32a, which can but need not be in the image plane of image receptor 26. A tilting mechanism 34, which also is in housing 14 or is otherwise coupled with receptor 26, can drive image receptor 26 in a tilting motion. Axes 30a and 32a extend left-right as seen in FIG. 1, and may but preferably do not coincide. For tomosynthesis imaging, breast platform 12 can be horizontal or can be at an angle to the horizontal, e.g., at an orientation similar to that for conventional MLO imaging in mammography. The system of FIG. 1 can be solely a mammography system, or solely a tomosynthesis system, or a "combo" system that can perform both mammography and tomosynthesis imaging. An example of such a combo system is been offered by the assignee hereof under the trade name Selenia Dimensions.

When the system is operated, image receptor 26 produces imaging information in response to illumination by imaging beam 22, and supplies it to image processor 34 for processing to generate breast x-ray images. A fluid control unit 36 connects with inflatable jacket 18 via conduit 36a, preferably through a quick-release snap-on connection 48. A system control and work station unit 38 controls the operation of the system and interacts with a user to receive commands and deliver information including processed-ray images.

Referring to FIGS. 1-6 (which are not to scale) for a more detailed illustration of breast immobilizer 20, compression paddle 16 typically is made of clear plastic and has a front wall 16a, a left side wall 16b, a right side wall 16c, and a bottom wall 16d having an underside 16e. Side walls 16b and 16c are supported by a bracket 16f that in turn is supported by support arm 28 for up-down movement along arm 28. For tilting relative to breast 10, paddle 16 is secured to bracket 16 with pins 16g (only the right pin is visible in FIG. 2) and is spring biased such that as paddle 16 presses against breast 10 the front end of paddle 16 lifts against the biasing force. If desirable, a compressible pad 40 may be placed on platform 12 to increase patient comfort, as in known for system offered by the common assignee. In addition, compression paddle 16 can move left-right as in the current system offered by the assignee under the trade name Selenia Dimensions.

An inflatable jacket 18 is releasably secured to compression paddle 16 and has a front wall 18a, a left side wall 18b, a right side wall 18c, and a bottom 18d having a top wall 18e facing the underside 16e of platform 16 and a bottom wall 18f. Bottom 18d thus comprises an inflatable chamber formed between walls 18e and 18f of jacket 18. This chamber 18d is in fluid flow communication with fluid control unit 36 via conduit 36a so it can be selectively inflated and, if desired, selectively deflated, to a desired pressure. A quick connect-release, snap-on connector 48 facilitates convenient connection of chamber 18d to fluid control unit 36 and disconnection from unit 36. If desired the bottom of jacket 18 can be divided into two or more chambers, such as chambers 18h and 18i, by a partition 18g, and separate conduits and connect/disconnect device (not shown) can be provided for each so that the two or more chambers can be inflated to desired pressures that may differ from each other.

Jacket 18 can be releasably secured to paddle 16 in any number of ways such that it can be easily attached and removed from paddle 16 and so that it will not undergo undesirable shifts relative to paddle 16 or the patient's skin while the breast is being immobilized and imaged.

Figure 3:
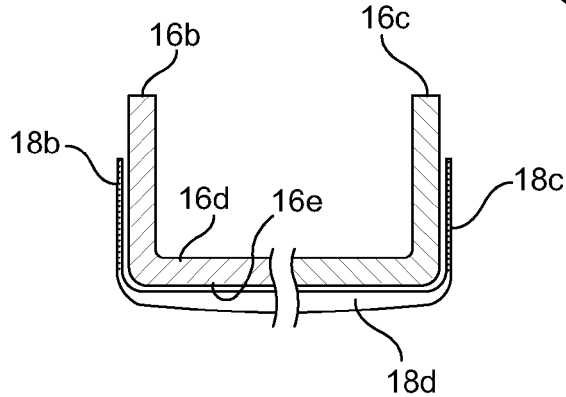
FIG. 3 illustrates schematically a section of the compression paddle with a paddle jacket secured thereto.

FIG. 3 illustrates one example, in which at least some of the surfaces of jacket 18 that face platform 16 are made of or coated with a material that adheres to platform 16 with a force that is sufficiently high to substantially prevent undesirable movement between platform 16 and jacket 18 but also sufficiently low to allow for easy removal of jacket 18 from paddle 16. Preferably at least the upper wall 18e of jacket 18 is made sticky for that purpose, but any one or more of the other walls can also be made sticky instead of or in addition to wall 16e. In this example of using adhesion to releasably secure jacket 18 to paddle 16, the front and side walls of jacket 18 preferably are shorter than the corresponding walls of paddle 16 but in the alternative can be the same height or even taller. The walls of jacket 18 can but need not be the same height; for example front wall 18a can have a lesser height compared with side walls 18b and 18c.

Figure 4:
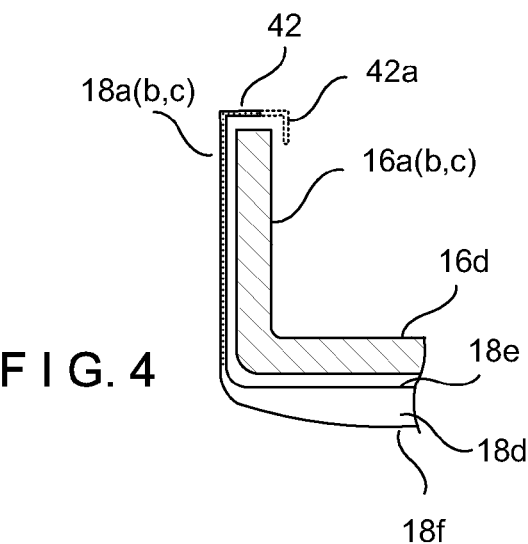
FIG. 4 illustrates schematically two examples of ways to releasably secure a paddle jacket to a compression paddle.

FIG. 4 illustrates other examples of releasably securing jacket 18 to paddle 16. In this example, at least one but preferably two or all three of front wall 18a and side walls 18b and 18c are provided with clipping members 42 that clip over the top of the respective wall of platform 16 and thus keep jacket 18 and platform 16 secured to each other. Clipping member 42 can be as shown in solid lines, or it can have an extension 42a as shown in dashed line. Jacket 18 typically is made of a plastic material such as vinyl that is somewhat stretchable and is dimensioned for a tight fit over platform 16 such that mechanical friction and perhaps some electrostatic force and inherent stickiness of the jacket material combine to maintain the jacket and platform from undesirable movement with respect to each other, but jacket 18 can still be easily peeled from paddle 16 by an operator so that a new jacket can be installed for the next patient if desired. Other example are contemplated, such as snap connections between the side walls of the jacket and the compression paddle, or other mechanical connections.

Figure 5:
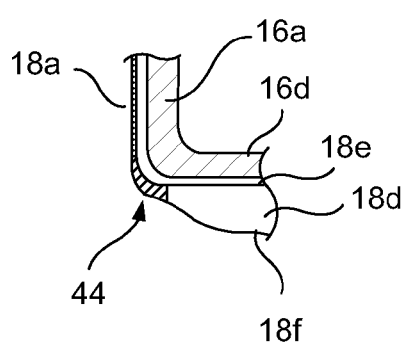
FIG. 5 illustrates schematically a seam in the paddle jacket.

Jacket 18 can be made of two layers of a material such a vinyl similar in chemical composition and thickness to that used for colostomy bags and even kitchen food bags and freezer bags. Preferably the two layers are fused or adhered to each other at the front and side walls of jacket 18, but not at the bottom 18d of jacket 18. Preferably, a seam 44 is formed, e.g., with adhesive material or by fusing, joining the two layers where jacket 18 adjoins the junction of the front and underside of platform 16 when jacket 18 is secured to platform 16, as illustrated in FIG. 5. Seam 42 can extend partly over front wall 16a and partly over underside 16e of platform 16, as illustrated (not to scale) in FIG. 5. Preferably, seam 42 is positioned such that the inflatable volume 18d of jacket 18 does not extent forward beyond front wall 16a of platform 16, so as not to push patient tissue away from platform 16.

Figure 6:
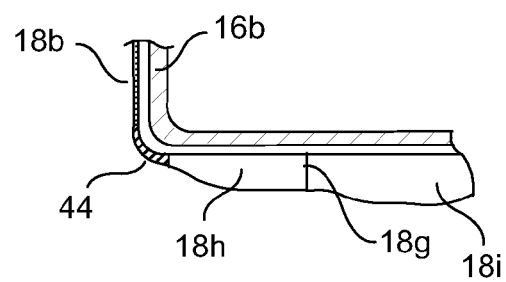
FIG. 6 illustrates a variant in which the bottom of the jacket comprises multiple chambers that can be pressurized to different degrees.

Referring to FIG. 6, the jacket's chamber 18d can comprise two or more sub-chambers, such as shown at 18h and 18i, each with a respective connection through a snap-on connector and a conduit to fluid control unit 36, so that each sub-chamber can be inflated to a desired pressure level under operator control or automated system control.

Fluid control unit 36 can be powered by an operator, using a hand-pump or a foot pump and appropriate manual or foot-controlled valves. Alternatively, electric or fluid-powered pumps can be used, with appropriate valves and interfaces such as buttons or switches that the operator controls. As another alternative, fluid control unit 36 can be fully automated such that inflation/deflation of jacket 18 is under control of station 38, when so enabled by an operator, and in response to events such as compression paddle 16 reaching a certain position relative to the patient's breast or to platform 12 or exerting a specified pressure on the patient's breast. The controls over inflation/deflation can be a part of or at least associated with unit 38.

In use, the mammography and/or tomosynthesis system is operated as known, for example as known for the systems offered by the common assignee under the commercial designations Selenia and Selenia Dimensions, except for the addition of inflatable paddle jacket 18. Thus, before patient imaging, a jacket 18 is secured to paddle 16 and connected to conduit 36 through a snap-on connector 48. With patient's breast 10 on platform 12 or pad 40, the technician lowers paddle 16 (with jacket 18 secured thereto) to begin compressing breast 10, while manually manipulating the breast to spread out breast tissue and pull tissue away from the patient's chest wall and into the x-ray field of view. In this process, the technician may control the degree of inflation of the jacket's chamber 18d before and/or after paddle 16 has been lowered to its final desired position by adding to and/or releasing fluid from chamber 18d. If chamber 18d comprises two or more sub-chambers, the technician may individually control the inflation of each in a similar manner. Once the technician or other health professional is satisfied with the position of breast 10, x-ray imaging can commence in a mammography and/or tomosynthesis mode, for example as known for said systems offered by the common assignee.

FIGS. 7-10 illustrate examples of an inflatable or inflated jacket 18 secured to a compression paddle in a breast imaging system. In FIG. 7, jacket 18 and paddle 16 are upside-down to better illustrate them and quick-release coupling 48. FIG. 8 illustrates paddle 16 and jacket 18 in a more typical orientation, and also illustrates a knob 80 that can be manually turned to move paddle 16 and its support left-right. FIG. 9 illustrates in perspective view a system in which components are identified by reference numeral used in FIG. 1 and described in connection with FIG. 1.

While specific examples have been described above, it should be clear that variations thereof are within the scope of the invention defined by the appended claim. As one of many possible examples, a similar inflatable jacket can be used on or over breast platform 12 in addition to or instead of using jacket 18 on compression paddle 16. In that example, such a jacket can be similarly secured to housing 14, or it can omit the side walls so that only a chamber similar to chamber 18d (or multiple sub-chambers) is present on breast platform 12, possibly with a front wall similar to front wall 18a but extending down along the front wall of housing 14

The invention claimed is:

1. An x-ray breast imaging system comprising:
a data acquisition unit comprising an x-ray source configured to selectively emit an imaging x-ray beam, an image receptor configured to receive said beam and produce a plurality of x-ray imaging information in response thereto, and a breast immobilizer between the source and the receptor;
said breast immobilizer comprising a breast platform configured to support a patient's breast for imaging with said beam and a compression paddle supported for movement toward the breast platform to compress the breast and away from the breast platform to release the breast;
said compression paddle having a front wall configured to be adjacent the patient's chest wall when the patient's breast is supported for said imaging, side walls extending transversely to the front wall, and an underside facing the breast platform;
a paddle jacket removably secured to the compression paddle, said jacket having a first flexible sheet and a second flexible sheet joined at a seam, wherein the first flexible sheet and the second flexible sheet extend along the underside of the paddle when secured to the paddle and form an inflatable chamber, and a fluid conduit that is in fluid flow communication with said chamber;
a fluid control unit releasably coupled with said conduit, said fluid control unit configured to selectively supply fluid to said chamber through said conduit and thereby selectively inflate and deflate the chamber, said fluid control unit further configured to maintain a substantially uniform internal pressure throughout an imaging procedure;
an image processor coupled with said image receptor and configured to receive said imaging information therefrom and produce x-ray images; and
a workstation and system control unit coupled with said data acquisition unit, said fluid control unit and said image processor, and configured to control operations thereof in response to operator inputs.

2. The breast imaging system of claim 1 in which said jacket further comprises front and side walls extending along said front and side walls of the compression paddle, respectively.

3. The breast imaging system of claim 2 in which one or more of the front and side walls of said jacket further comprise clipping members configured to releasably clip upper portions of one or more of the front and side walls of said compression paddle, respectively.

4. The breast imaging system of claim 3 in which one or more of the front and side walls of said jacket extend to above one or more of the front and side walls of the compression paddle and terminate in said clipping members.

5. The breast imaging system of claim 1 in which one or more of the bottom and front and side walls of said jacket include adhesive material such that said jacket is releasably adhered to said compression paddle.

6. The breast imaging system of claim 1 in which an exterior of one or more of the front wall and bottom of said jacket include a friction-enhancing surface configured to enhance friction between said surface and a patient's skin.

7. The breast imaging system of claim 6 in which said friction enhancing surface comprises a jacket surface with a sticky substance therein or thereon.

8. The breast imaging system of claim 1 in which at least a bottom of said jacket is substantially transparent to visible light, whereby a technician adjusting a patient's breast for imaging can visualize the breast through said jacket.

9. The breast imaging system of claim 1 in which said jacket comprises a vinyl material.

10. The breast imaging system of claim 1 in which said jacket includes markings of a material that attenuate said x-ray beam sufficiently to be visible in said x-ray images.

11. The breast imaging system of claim 1 in which said chamber in divided into two or more sub-chambers that are individually inflatable.

12. The breast imaging system of claim 1 in which said jacket comprises two layers of flexible sheet material that are seamed at least at a portion that extends along a junction between the front wall and the underside of the compression paddle.

13. The breast imaging system of claim 1 in which said jacket includes a front wall and side walls that are not inflatable.

14. The breast imaging system of claim 13 in which said front wall of said jacket is shorter vertically than the front wall of the compression paddle.

15. A method of imaging a patient's breast with x-rays comprising:
supporting the breast on a breast platform and compressing the breast with a compression paddle through a paddle jacket that comprises an inflatable bottom extending along a bottom of a compression paddle and front and side walls extending respectively along front and side walls of the compression paddle, and wherein the inflatable bottom comprises a plurality of sheet layers joined at a seam;

selectively inflating and deflating the inflatable bottom of said jacket against the patient's breast;

imaging the compressed breast with x-ray;

maintaining a substantially uniform internal pressure of said inflatable bottom throughout an imaging procedure; and generating x-ray images of the breast.

16. The method of claim 15 further comprising removably securing said jacket to the compression paddle before compressing the patient's breast.

17. The method of claim 15 in which said securing comprises adhering one or more of the bottom and the walls of the jacket to one or more of an underside and the respective walls of the compression paddle.

18. The method of claim 15 in which said securing comprises clipping one or more of the front and side walls of the jacket to one or more respective walls of the compression paddle.

19. The method of claim 15 further comprising individually inflating two or more portions of the jacket bottom.

20. The method of claim 15 further comprising providing one or more exterior portions of said jacket with friction-enhancing surfaces to increase friction with the patient's skin.

21. An inflatable compression paddle jacket configured to be releasably secured to a compression paddle configured to compresses a patient's breast for x-ray imaging, said paddle having an underside, a front wall and left and right side walls, said jacket comprising:

a bottom comprising one or more inflatable chambers, said bottom having an upper sheet surface configured to face the underside of said compression paddle when the jacket is secured to the paddle, and a lower sheet surface configured to face away from the underside of said compression paddle when the jacket is secured to the paddle;

one or more of a front wall, a left side wall and a right side wall configured to face one or more of the respective wall of the compression paddle when the jacket is secured to the paddle, wherein at least one of the front wall, the left side wall, and the right side wall form a seam joining the upper sheet surface and the lower sheet surface; and a conduit connecting an interior of the one or more of the inflatable chambers for fluid flow from an exterior thereof for selectively inflating and deflating the one or more chambers of the jacket against the patient's breast, said conduit configured to maintain a substantially uniform internal pressure of said one or more inflatable chambers throughout an imaging procedure.

22. The inflatable jacket of claim 21 in which said upper sheet surface and said lower sheet surface are seamed at selected portions thereof to form said one or more inflatable chambers.

23. The inflatable jacket of claim 22 in which said upper sheet surface and said lower sheet surface are seamed at one or more seams that extend at least along a lower portion of the front wall of said compression paddle when the jacket is secured to the paddle for x-ray imaging of the patient's breast.

24. The inflatable jacket of claim 22 in which said upper sheet surface and said lower sheet surface are seamed at one or more seams that extend at least along a front portion of the underside of said paddle when the jacket is secured to the paddle for x-ray imaging of the patient's breast.

25. The inflatable jacket of claim 22 in which said upper sheet surface and said lower sheet surface are seamed at one or more seams that extend at least along a junction of the front wall and the underside of said paddle when the jacket is secured to the paddle for x-ray imaging of the patient's breast.

26. The inflatable jacket of claim 22 including one or more clipping portions at the one or more of the walls of the jacket, said clipping portions configured to engage one or more of the respective walls of the compression paddle when the jacket is secured to the paddle for x-ray imaging of the patient's breast.

27. The inflatable jacket of claim 22 including sticky surfaces at a one or more of the walls and bottom of the jacket, said sticky surfaces being configured to releasably adhere to facing surfaces of said compression paddle when the jacket is secured to the paddle for x-ray imaging of the patient's breast.

* * * * *